(12) United States Patent
Rogers et al.

(10) Patent No.: US 9,751,841 B2
(45) Date of Patent: Sep. 5, 2017

(54) PROCESS FOR THE PREPARATION OF CHALCOGENE COMPOUNDS

(75) Inventors: Robin Don Rogers, Belfast Antrim (GB); John Holbrey, Belfast Antrim (GB); Hector Rodriguez, Belfast Antrim (GB)

(73) Assignee: Petroliam Nasional Berhad (MY)

( * ) Notice: Subject to any disclaimer, the term of this patent is extended or adjusted under 35 U.S.C. 154(b) by 196 days.

(21) Appl. No.: 13/263,192

(22) PCT Filed: Mar. 30, 2010

(86) PCT No.: PCT/GB2010/050550
§ 371 (c)(1),
(2), (4) Date: Dec. 20, 2011

(87) PCT Pub. No.: WO2010/116166
PCT Pub. Date: Oct. 14, 2010

(65) Prior Publication Data
US 2012/0108822 A1 May 3, 2012

(30) Foreign Application Priority Data
Apr. 6, 2009 (GB) .................................. 0905895.9

(51) Int. Cl.
*C07D 233/42* (2006.01)

(52) U.S. Cl.
CPC .......... *C07D 233/42* (2013.01); *Y02P 20/582* (2015.11)

(58) Field of Classification Search
CPC .................................................... C07D 233/42
USPC ...................................................... 548/325.1
See application file for complete search history.

(56) References Cited

U.S. PATENT DOCUMENTS

| 5,104,993 A | 4/1992 | Arduengo, III | |
| 5,182,405 A | 1/1993 | Arduengo, III | |
| 2007/0142646 A1* | 6/2007 | Maase et al. | 548/335.1 |
| 2008/0171883 A1* | 7/2008 | Arduengo | 548/325.1 |

FOREIGN PATENT DOCUMENTS

CN 101029026 A 9/2007

OTHER PUBLICATIONS

Williams et al., Journal of Chemical Crystallography, 33(5/6); 465-472 (2003).*
Cetinkaya et al., Arzneim-Forsch./Drug Res., 46(II); 1154-1158 (1996).
Kuhn et al., CHBEAM, 126(9); 1961-2156 (1993).
Peng et al., Chinese Journal of Catalysis, 28(6); 495-497 (2007). (English translation of abstract only).
Wolfe et al., Eur. J. Org. Chem., 2825-2838 (2007).
Kucukbay et al., Il Farmaco, 58; 431-437 (2003).
Gouriprasanna et al., J. Am. Chem. Soc., 127(43); 15207-15217 (2005).
Arduengo et al., J. Am. Chem. Soc., 119(52); 12742-12749 (1997).
Shevtsov et al., Commun., 16(4); 218-220 (2006).
Organic Syntheses: An Annual Publication of Satisfactory Methods for the Preparation of Organic Chemicals, 64; 92-94 (1986).
Tao et al., Synthetic Communications, 37; 399-408 (2007).
International Search Report, PCT/GB2010/050550, dated Mar. 25, 2011.

* cited by examiner

*Primary Examiner* — Yong Chu
*Assistant Examiner* — Sonya Wright
(74) *Attorney, Agent, or Firm* — Lerner, David, Littenberg, Krumholz & Mentlik, LLP

(57) ABSTRACT

The present invention is a novel process for the preparation of chalcogenone compounds by conversion of ionic liquids and salts comprising nitrogen-containing heterocyclic cations and basic anions to the corresponding nitrogen-containing heterocyclic chalcogenones by reaction with elemental chalcogens.

27 Claims, No Drawings

PROCESS FOR THE PREPARATION OF CHALCOGENE COMPOUNDS

CROSS REFERENCE TO RELATED APPLICATIONS

The present application is a national phase entry under 35 U.S.C. §371 of International Application No. PCT/GB2010/050550 filed Mar. 30, 2010, published in English, which claims priority from United Kingdom application GB 0905895.9, filed Apr. 6, 2009, the entire contents of which are herein incorporated by reference.

The present invention relates to a novel process for the preparation of chalcogenone compounds. More specifically, the present invention relates to a process for the conversion of ionic liquids and salts comprising nitrogen-containing heterocyclic cations and basic anions to the corresponding nitrogen-containing heterocyclic chalcogenones by reaction with elemental chalcogens.

Heterocyclic chalcogenones are valuable chemicals that have applications in a wide range of technical fields. One class of heterocyclic chalcogenones are imidazole-2-thiones. Imidazole-2-thiones are known to exhibit pharmaceutical activity, and have been clinically used for the treatment of several diseases. In addition, imidazole-2-thione C-nucleosides have been used as synthetic precursors to azidonucleosides and fluoronucleosides which possess anti-AIDS activity.

In addition to their clinical applications, imidazole-2-thiones have also been used industrially as rubber antioxidants and as accelerators of rubber vulcanisation. A further application of imidazole-2-thiones is as light-sensitive photographic and photothermographic materials. Furthermore, 1,3-disubstituted imidazole-2-thiones are a versatile class of catalysts which have been used, for example, in the cross-linking of epoxy functionalised materials and isocyanate functionalised materials to form crosslinked resin coatings.

Imidazole-2-selenones are a closely related class of compounds which have been identified as potential anti-hyperthyroid drugs (Roy, G., et al., J. Amer. Chem. Soc., 2005, volume 127, pages 15207-15217), and as catalysts for carbonylation reactions of amines (Li, P., et al., Cuihua Xuebao, 2007, volume 28, pages 495-497).

A further related class of compounds are imidazole-2-tellurinones and benzimidazole-2-tellurinones, which have been shown to have antimicrobial activity against Gram-positive bacteria (Kucukbay, H., et al., Farmaco, 2003, volume 58, pages 431-437; and Kucukbay, H., et al., Arzneimittel-Forschung, 1996, volume 46, pages 1154-1158).

In one known method for the preparation of imidazole-2-thiones, imidazolium salts are reacted with a base and elemental sulfur either sequentially (to form a carbene intermediate), or in a single step (via a transient carbine species). The bases that have been used in the known method include potassium tert-butoxide (in sequential reactions), or potassium carbonate and sodium methoxide (in single step reactions) (see Benac, et al., Org. Syn., 1986, volume 64, pages 92-95; and U.S. Pat. No. 5,104,993). A disadvantage of these known methods is that stoichiometric quantities of inorganic salt by-products are formed and must be separated from the imidazole-2-thione products in a separate step. In addition, the reaction is conducted in the presence of an organic solvent, such as pentane or methanol.

More recently it has been found that, by using microwave irradiation, imidazolium salts can be converted into the corresponding imidazole-2-thiones using softer bases such as potassium thioacetate or potassium thiocyanate (Tao, X.-L., et al., Syn. Commun., 2007, volume 37, pages 399-408), or using potassium carbonate in acetone (CN 1001-1397 20060301), however these approaches still require the use of an external base, leading to the formation of worthless inorganic by-products.

In addition, a solvent-free, single-step process for the production of imidazole-2-thiones has recently been reported (US 2008/0171883). This method involves the reaction of an imidazolium salt with elemental sulfur in the presence of an external base. Thus, although the problem of using an organic solvent is avoided, the process still requires a typically solid external base, which generates undesired inorganic by-products.

The preparation of imidazole-2-tellurinones by the reaction of nitrogen-containing heterocyclic carbenes with elemental tellurium in solution has also been described (Kuhn et al., Chemische Berichte, 1993, volume 126, pages 2047-2049; and Arduengo et al., J. Amer. Chem. Soc., 1997, volume 119, pages 12742-12749).

The present invention is based on the surprising discovery that organic salts comprising certain nitrogen-containing heterocyclic cations and anions which are the conjugate bases of weak acids may be reacted with elemental chalcogens in the absence of additional bases so as to form heterocyclic chalcogenones. This represents a significant advantage over known processes for the synthesis of heterocyclic chalcogenones as the cost, the additional process steps, and the hazard to operators associated with the use of basic reagents are all avoided. Furthermore, the reaction works effectively in the absence of additional solvents, particularly where the salt is molten (i.e. an ionic liquid) at the operating temperature of the process.

It will be understood that in the context of the present invention, chalcogenone compounds are compounds that include at least one thiocarbonyl, selenocarbonyl, or tellurinocarbonyl moiety. In addition, in the context of the present invention, elemental chalcogens include elemental sulfur, elemental selenium, or elemental tellurium.

In a first aspect, the present invention provides a process for the preparation of heterocyclic chalcogenone compounds comprising reacting an elemental chalcogen selected from elemental sulfur, elemental selenium and elemental tellurium with an ionic liquid or salt having the formula:

wherein: [Cat$^+$] represents one or more heterocyclic cationic species of the general formula (1) having adjacent carbon and nitrogen atoms:

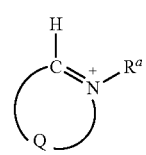

(1)

wherein R$^a$ represents a C$_1$ to C$_{30}$ straight chain or branched alkyl group, a C$_3$ to C$_8$ cycloalkyl group, a C$_6$ to C$_{10}$ aryl group, a C$_1$ to C$_{30}$ alkaryl group, or a C$_1$ to C$_{30}$ aralkyl group;

wherein said alkyl, cycloalkyl, aryl, alkaryl or aralkyl groups are unsubstituted or substituted;

Q represents a linking moiety, which may be saturated or unsaturated, and which may be substituted or unsubstituted; and which when taken together with the adjacent carbon and nitrogen atoms forms a heterocyclic ring comprising 5 to 10 ring atoms; and

[X⁻] represents one or more anionic species selected from conjugate bases of acids having the formula [H⁺X⁻] and having a p$K_a$ value greater than 2.5; and wherein the reaction is conducted in the absence of an additional base.

In a preferred embodiment of the invention, the elemental chalcogen is selected from sulfur and selenium. Most preferably the elemental chalcogen is sulfur. No specific pretreatment of the elemental chalcogen is necessary, though in some cases it may be preferable if the chalcogen is in powdered form.

It will be appreciated that in the heterocyclic cations represented by the general formula (1), Q may be any linking group that, when together with the adjacent carbon and nitrogen atoms, gives rise to a stable heterocyclic cation comprising a ring of 5 to 10 atoms. More preferably Q is a linking group that, when taken together with the adjacent carbon and nitrogen atoms, gives rise to a stable heterocyclic cation comprising a ring of 5 or 6 atoms.

In one embodiment of the invention, Q may comprise a chain of 3 to 8 carbon atoms. In another embodiment of the invention, Q may comprise a chain of 3 to 8 atoms selected from carbon, nitrogen, oxygen and sulfur, provided said chain of 3 to 8 atoms gives rise to a stable heterocyclic cation.

As noted above, Q may be saturated or unsaturated. In a preferred embodiment Q is unsaturated such that Q when taken together with the adjacent carbon and nitrogen atoms forms an aromatic ring. It will be appreciated by the skilled person that aromatic rings may be represented in two canonical forms. For the purposes of the present invention, it is necessary that at least one of the canonical forms of an aromatic heterocyclic cation may be represented by general formula (1).

Also as noted above, Q may be substituted or unsubstituted. As used herein, the term unsubstituted means that any vacant valence sites on the chain of atoms forming Q are occupied by hydrogen atoms. Suitable substituents include $C_1$ to $C_{30}$ straight chain or branched alkyl groups, $C_3$ to $C_8$ cycloalkyl groups, $C_6$ to $C_{10}$ aryl groups, $C_7$ to $C_{30}$ alkaryl groups, $C_7$ to $C_{30}$ aralkyl groups, and $C_1$ to $C_{30}$ alkoxy groups, which may be substituted or unsubstituted. Alternatively, or in addition, Q may be fused to another ring via two adjacent atoms in the chain of atoms that forms Q, wherein the other ring may be a saturated or unsaturated carbocyclic or heterocyclic ring. Where Q is fused to another ring via two adjacent atoms in the chain of atoms that forms Q, said other ring may also be substituted or unsubstituted.

Without being bound by any particular theory of operation, it is believed that the heterocyclic cation of formula (1) is deprotonated by the basic anion of the ionic liquid or salt to form an intermediate carbene (2), which then reacts with an elemental chalcogen to form a chalcogenone of formula (3), as shown in Mechanism 1.

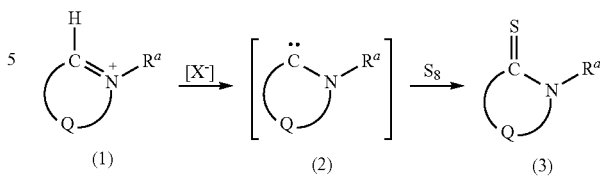

Mechanism 1

In a preferred embodiment of the invention, the general formula (1) represents a heterocyclic cationic species selected from the group consisting of: imidazolium, pyrazolium, 1,2,4-triazolium, oxazolium, isoxazolium, thiazolium, isothiazolium, 1,2,4-oxadiazolium, 1,2,5-oxadiazolium, 1,3,4-oxadiazolium, 1,2,3,4-oxatriazolium, 1,2,3,5-oxatriazolium, 1,2,4-thiadiazolium, 1,2,5-thiadiazolium, 1,3,4-thiadiazolium, 1,2,3,4-thiatriazolium, 1,2,3,5-thiatriazolium, pyridinium, pyridazinium, pyrimidinium, pyrazinium, 1,2,3-triazinium, 1,2,4-triazinium, 1,3,5-triazinium, 1H-indazolium, benzimidazolium, benzisoxazolium, benzoxazolium, benzothiazolium, benzisothiazolium, quinolinium, isoquinolinium, cinnolinium, quinazolinium, quinoxalinium, and phthalazinium.

More preferably, general formula (1) represents a heterocyclic cationic species selected from the group consisting of: imidazolium, pyrazolium, 1,2,4-triazolium, oxazolium, thiazolium, pyridinium, pyridazinium, pyrimidinium, pyrazinium, benzimidazolium, quinolinium, and isoquinolinium.

Still more preferably, general formula (1) represents a heterocyclic cationic species selected from the group consisting of:

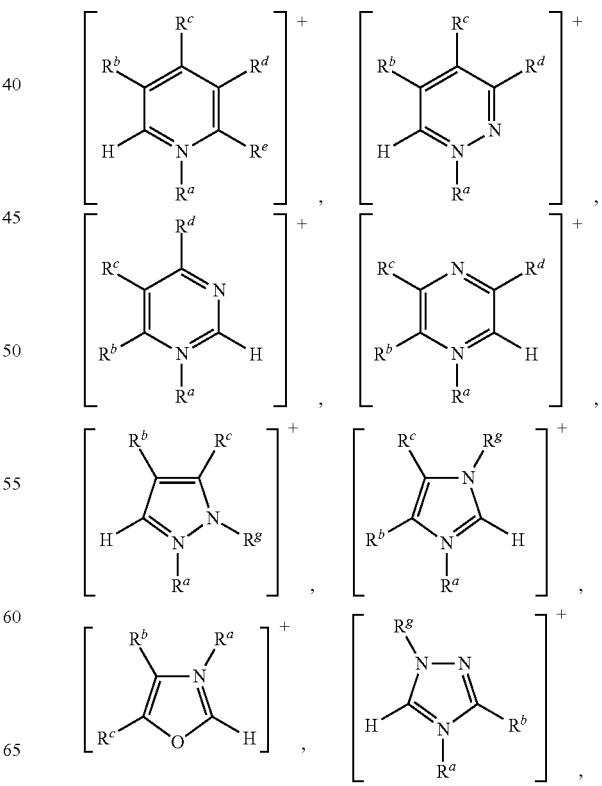

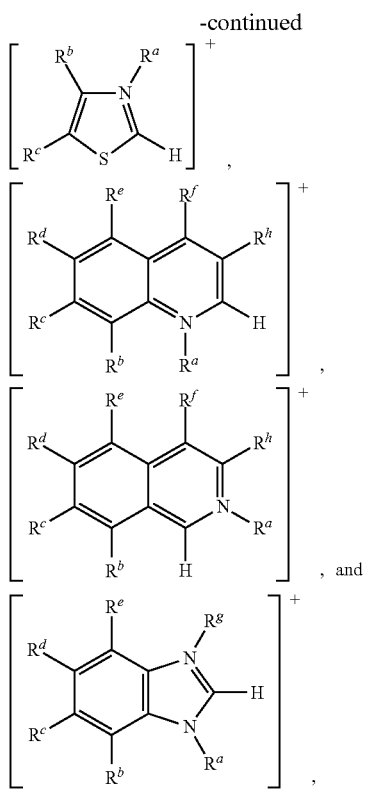

wherein: $R^a$, $R^b$, $R^c$, $R^d$, $R^e$, $R^f$, $R^g$ and $R^h$ are each independently selected from a $C_1$ to $C_{30}$, straight chain or branched alkyl group, a $C_3$ to $C_8$ cycloalkyl group, a $C_6$ to $C_{10}$ aryl group, $C_1$ to $C_{30}$ alkaryl group, a $C_1$ to $C_{30}$ aralkyl group, and wherein $R^b$, $R^c$, $R^d$, $R^e$, $R^f$ and $R^h$ may also be hydrogen or $C_1$ to $C_{30}$ alkoxy, or any two of $R^b$, $R^c$, $R^d$, $R^e$, $R^f$ and $R^h$ attached to adjacent carbon atoms may form a methylene chain —$(CH_2)_q$— wherein q is from 3 to 6; and wherein said alkyl, cycloalkyl, aryl, alkaryl, aralkyl or alkoxy groups or said methylene chain are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —$NO_2$, —$CO_2(C_1$ to $C_6)$alkyl, —OC(O)$R^x$, —C(O)$R^x$, —C(S)$R^x$, —$CS_2(C_1$ to $C_6)$alkyl, —SC(S)$R^x$, —S(O)($C_1$ to $C_6$)alkyl, —S(O)O ($C_1$ to $C_6$)alkyl, —OS(O)($C_1$ to $C_6$)alkyl, —S($C_1$ to $C_6$)alkyl, —S—S($C_1$ to $C_6$)alkyl, —$NR^x$C(O)$NR^yR^z$, —$NR^x$C(O)O($C_1$ to $C_6$)alkyl, —OC(O)$NR^yR^z$, —$NR^x$C(S)O($C_1$ to $C_6$)alkyl, —OC(S)$NR^yR^z$, —$NR^x$C(S)S($C_1$ to $C_6$)alkyl, —SC(S)$NR^yR^z$, —$NR^x$C(S)$NR^yR^z$, —C(O)$NR^yR^z$, —C(S)$NR^yR^z$, —$NR^yR^z$, or a heterocyclic group, wherein $R^x$, $R^y$ and $R^z$ are independently selected from hydrogen or $C_1$ to $C_6$ alkyl.

Preferably, $R^a$, $R^b$, $R^c$, $R^d$, $R^e$, $R^f$, $R^g$, and $R^h$ are each independently selected from a $C_1$ to $C_{10}$ straight chain or branched alkyl group, a $C_1$ to $C_{10}$ alkoxyalkyl group, a $C_3$ to $C_6$ cycloalkyl group, a $C_6$ aryl group, a $C_7$ to $C_{10}$ alkaryl group, or a $C_7$ to $C_{10}$ aralkyl group; and $R^b$, $R^c$, $R^d$, $R^e$, $R^f$ and $R^h$ may also be hydrogen or $C_1$ to $C_{10}$ alkoxy or any two of $R^b$, $R^c$, $R^d$, $R^e$, $R^f$ and $R^h$ attached to adjacent carbon atoms may form a methylene chain —$(CH_2)_q$—, wherein q is from 3 to 6.

More preferably, $R^a$, $R^b$, $R^c$, $R^d$, $R^e$, $R^f$, $R^g$, and $R^h$ are each independently selected from a $C_1$ to $C_6$ straight chain or branched alkyl group, a $C_1$ to $C_6$ alkoxyalkyl group, a $C_3$ to $C_6$ cycloalkyl group, a $C_6$ aryl group, a $C_7$ to $C_{10}$ alkaryl group, or a $C_7$ to $C_{10}$ aralkyl group; and $R^b$, $R^c$, $R^d$, $R^e$, $R^f$ and $R^h$ may also be hydrogen or $C_1$ to $C_6$ alkoxy.

Suitable $C_1$ to $C_6$ alkyl groups include methyl, ethyl, n-propyl, iso-propyl, butyl, sec-butyl, iso-butyl, n-pentyl, iso-pentyl, hexyl, 2-ethylbutyl, 2-methylpentyl. Suitable $C_1$ to $C_6$ alkoxy groups include the foregoing alkyl groups bonded through an oxygen atom.

$R^a$ is preferably selected from $C_1$ to $C_{15}$ straight chain or branched alkyl, $C_1$ to $C_{15}$ alkoxyalkyl, or $C_6$ to $C_{10}$ aryl. More preferably $R^a$ is selected from $C_1$ to $C_{10}$ straight chain or branched alkyl or $C_1$ to $C_{10}$ alkoxyalkyl; still more preferably $C_1$ to $C_8$ straight chain or branched alkyl or $C_1$ to $C_8$ alkoxyalkyl; still more preferably $C_1$ to $C_8$ straight chain or branched alkyl or $C_1$ to $C_8$ alkoxyalkyl; more preferably $C_1$ to $C_6$ straight chain or branched alkyl or $C_1$ to $C_6$ alkoxyalkyl; and most preferably $R^a$ is $C_1$ to $C_6$ straight chain or branched alkyl.

In the heterocyclic cations comprising an $R^g$ group, $R^g$ is preferably selected from $C_1$ to $C_{10}$ straight chain or branched alkyl, more preferably $C_1$ to $C_{15}$ straight chain or branched alkyl, and most preferably $R^g$ is a methyl group.

Most preferably, $R^b$, $R^c$, $R^d$, $R^e$, $R^f$, and $R^h$ are each hydrogen.

In a further preferred embodiment, the general formula (1) represents a heterocyclic cationic species selected from the group consisting of:

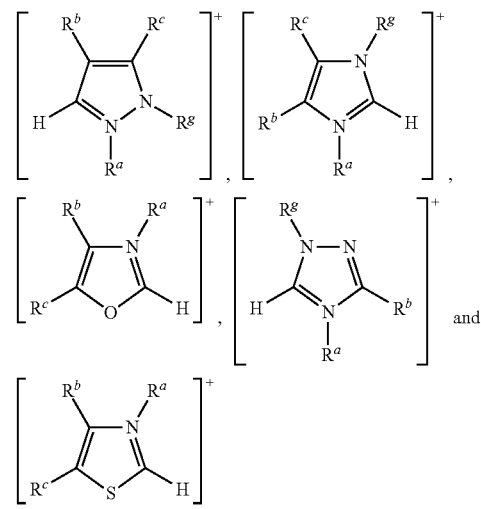

wherein: $R^a$, $R^b$, $R^c$ and $R^g$ are as defined above.

Still more preferably, the general formula (1) represents a heterocyclic cationic species selected from:

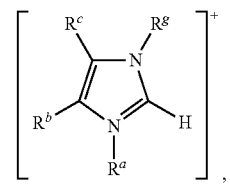

wherein: $R^a$, $R^b$, $R^c$, and $R^g$ are as defined above.

Still more preferably, the general formula (1) represents a heterocyclic cationic species selected from:

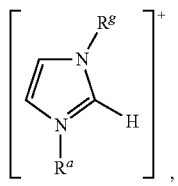

wherein: $R^a$ and $R^g$ are as defined above.

Most preferably, general formula (1) represents a heterocyclic cationic species selected from:

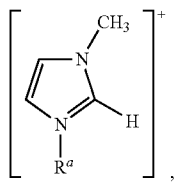

wherein: $R^a$ is a $C_1$ to $C_6$ straight chain or branched alkyl group.

In a further preferred embodiment, the general formula (1) represents a heterocyclic cationic species selected from:

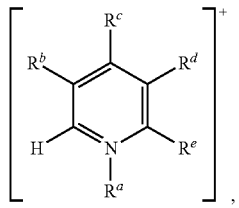

wherein: $R^a$, $R^b$, $R^c$, $R^d$ and $R^e$ are as defined above.

More preferably, the general formula (1) represents a heterocyclic cationic species selected from:

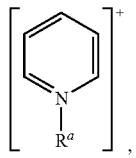

wherein: $R^a$ is a $C_1$ to $C_6$ straight chain or branched alkyl group.

In a further preferred embodiment, the general formula (1) represents a heterocyclic cationic species that forms a carbene having two ring heteroatoms adjacent to the carbene carbon. Examples of suitable heterocyclic cationic species in accordance with this embodiment of the invention include: imidazolium, 1,2,4-triazolium, oxazolium, thiazolium, 1,2,4-oxadiazolium, 1,3,4-oxadiazolium, 1,2,3,4-oxatriazolium, 1,2,3,5-oxatriazolium, 1,2,4-thiadiazolium, 1,3,4-thiadiazolium, 1,2,3,4-thiatriazolium, 1,2,3,5-thiatriazolium, pyrimidinium, 1,2,4-triazinium, 1,3,5-triazinium, benzimidazolium, benzoxazolium, benzothiazolium, and quinazolinium.

More preferably, in accordance with this embodiment of the invention, the general formula (1) represents a heterocyclic cationic species selected from:

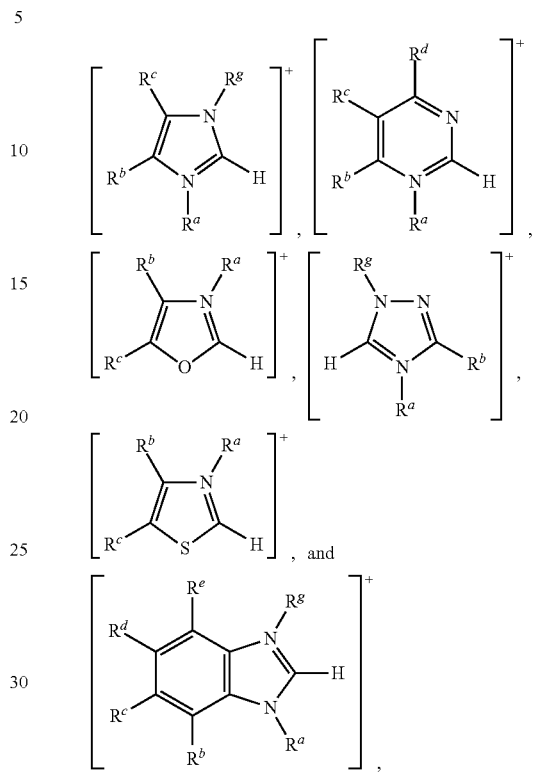

wherein: $R^a$, $R^b$, $R^c$, $R^d$ and $R^e$ are as defined above.

In accordance with the present invention, [$X^-$] represents an anion which is the conjugate base of a weak acid having a p$K_a$ of greater than 2.5, more preferably greater than 3.5, and most preferably greater than 4.5.

Examples of suitable anions include carboxylate ions, such as [$CH_3CO_2$]$^-$, [$CH_3CH_2CO_2$]$^-$, [$CH_3(CH_2)_2CO_2$]$^-$, [$PhCO_2$]$^-$.

Further suitable anions include [$CN$]$^-$, [$CO_3$]$^{2-}$, [$HCO_3$]$^-$, [$OH$]$^-$, [$SH$]$^-$, and [$NO_2$]$^-$.

The present invention is not limited to the reaction of ionic liquids and salts comprising anions having only a single charge. As noted above, anions such as [$CO_3$]$^{2-}$ may be used. Thus, the formula [$Cat^+$][$X^-$] is intended to encompass ionic liquids and salts comprising, for example, doubly or triply charged anions. The relative stoichiometric amounts of [$Cat^+$] and [$X^-$] in the ionic liquid or salt are therefore not fixed, but can be varied to take account of anions with multiple charges. For example, the formula [$Cat^+$][$X^-$] should be understood to include ionic liquids and salts having the formulae [$Cat^+$]$_2$[$X^{2-}$] or [$Cat^+$]$_3$[$X^{3-}$], for example It will also be appreciated that the present invention is not limited to ionic liquids comprising a single cation and a single anion. Thus, [$Cat^+$] may, in certain embodiments, represent two or more cations, such as a statistical mixture of 1,3-dimethylimidazolium, 1-ethyl-3-methylimidazolium and 1,3-diethylimidazolium. Similarly, [$X^-$] may, in certain embodiments, represent two or more anions, such as a mixture of acetate ([$CH_3CO_2$]$^-$,) and benzoate ([$PhCO_2$]$^-$).

If desired, the reaction may be conducted in the presence of a solvent which is compatible with the ionic liquids and salt and the chalcogenone product, and which is inert towards the carbene intermediate. The use of a solvent may be appropriate where it is desired to dissolve a solid salt or to modify the viscosity of an ionic liquid. Suitable solvents for this purpose are non-basic aprotic polar solvents, such as acetonitrile, dimethylsulfoxide, dimethylformamide and sulfolane (tetrahydrothiophene 1,1-dioxide). Preferably, however, the reaction is conducted in the absence of an additional solvent. Preferably, the reaction is conducted in the substantial absence of protic solvents, such as water and alcohols, as these have been found to retard the progress of the reaction.

Where [Cat$^+$][X$^-$] represents a salt which is solid at the operating temperature and pressure of the reaction, the reaction may be conducted as a solid state, solvent-free reaction. In this embodiment of the invention, the solid [Cat$^+$][X$^-$] and the solid elemental chalcogen are preferably combined in powdered form. Alternatively, where [Cat$^+$][X$^-$] represents an ionic liquid at the operating temperature and pressure of the reaction, the reaction may be conducted using a slurry of the solid chalcogen in the ionic liquid.

Most preferably, the process of the present invention is conducted under conditions of temperature above the melting point of [Cat$^+$][X$^-$] (such that [Cat$^+$][X$^-$] is an ionic liquid) and in the absence of an additional solvent. Thus, [Cat$^+$][X$^-$] preferably has a melting point below 100° C., and more preferably [Cat$^+$][X$^-$] has a melting point below 25° C.

Examples of [Cat$^+$][X$^-$] which are liquid at ambient temperature and pressure are 1-ethyl-3-methylimidazolium hydroxide and 1-butyl-3-methylimidazolium acetate. An example of [Cat$^+$][X$^-$] having a melting point above ambient temperature at ambient pressure is 1,3-diisopropylimidazolium acetate.

The process of the present invention is preferably conducted at a temperature of from −10° C. to 150° C., and more preferably from 25° C. to 100° C., for example from 70° C. to 80° C. Where the reaction is heated above ambient temperature, heating may be accomplished using any suitable method. For example, the reaction may be heated using conventional thermal methods, microwave heating or employing other heat sources such as ultrasound or infrared radiation.

The process of the present invention is preferably conducted at a pressure of from 10,000 to 1,000,000 kPa (0.1 to 10 bar), more preferably 50,000 to 500,000 kPa (0.5 to 5 bar), and most preferably the process is conducted at ambient pressure (approximately 100,000 kPa).

In accordance with the present invention, the ionic liquid or salt is preferably reacted with the elemental chalcogen in a molar ratio, based on atoms of the chalcogen of from 1:100 to 100:1, more preferably from 1:10 to 10:1, still more preferably from 1:5 to 5:1, and most preferably the ionic liquid or salt is reacted with the elemental chalcogen in a molar ratio of about 1:1.

The process of the invention is conducted over a suitable timescale to obtain quantitative or near quantitative (e.g. greater than 95%) conversion of the starting ionic liquid or salt to the chalcogenone product. It will be appreciated that the rate of reaction will vary according to the salt or ionic liquid and the chalcogen than are used. In addition, other reaction parameters such as temperature, pressure and the choice of solvent, if any, may also influence the reaction rate. However, quantitative or near quantitative conversion of the starting ionic liquid or salt to the chalcogenone product is preferably obtained in less than 24 hours, more preferably less than 5 hours, and most preferably less than 1 hour.

The process of the present invention may be illustrated by reference to the reaction of an imidazolium salt with elemental sulfur ($S_8$). As shown in Mechanism 2, the imidazolium cation (4) reacts with the basic anion [X$^-$] to form a carbene intermediate (5), which subsequently reacts with the elemental sulfur to form the imidazole-2-thione (6).

Mechanism 2

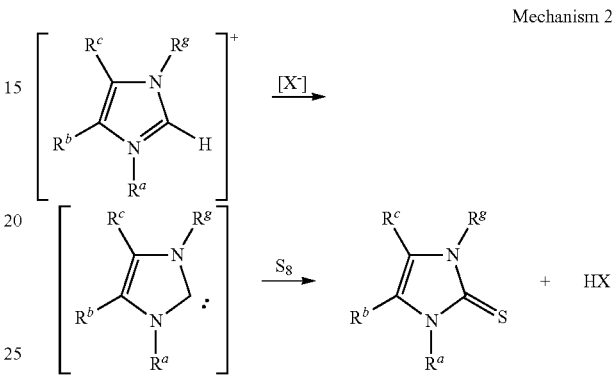

It will be observed that the only by-product of the reaction is the conjugate acid H$^+$X$^-$ of the basic anion [X$^-$]. The acid H$^+$X$^-$ may be recycled during the production of further [Cat$^+$][X$^-$], using any suitable method. For example, a process for the production of imidazolium acetate ionic liquids has been reported by Maase, et al. (US Patent Application Publication No. US 2007/0142646).

Thus, in a preferred embodiment of the invention the production of the ionic liquid or salt [Cat$^+$][X$^-$] is integrated with the synthesis of the chalcogenone. Thus, the acid by-product of the chalcogenone preparation is completely recycled, and no net by-product is formed in the chalcogenone preparation.

In a further aspect of the invention, the chalcogenone product may be isolated by solvent extraction. Unreacted [Cat$^+$][X$^-$] is soluble in water and some organic solvents, as is the acid (H$^+$X$^-$) by-product of the reaction; whereas the chalcogenone is insoluble in water and soluble in some organic solvents. Since sulfur is insoluble in both water and the aforementioned solvents, sequential extractions using water and organic solvents may be used to isolate the chalcogenone product from unreacted ionic liquid, unreacted chalcogen, and the acid by-product of the reaction. Different strategies for this can be envisioned, depending on whether the organic solvent is miscible with water.

If the organic solvent is immiscible with water, then a liquid-liquid extraction accompanied by filtration of sulfur may be suitable. Alternatively, if the organic solvent is miscible with water, addition of the organic solvent to the reaction mixture followed by filtration of the insoluble sulfur, removal of the organic solvent, and subsequent liquid-liquid extraction using water and a water immiscible organic solvent is suitable.

The presence of the acid by-product of the reaction in the reaction medium has been observed to slow the rate of reaction, such that in some cases an equilibrium may be reached at which the ionic liquid or salt is not fully converted to the chalcogenone product. Under such circumstances, the starting materials are fully recyclable into the reaction such that no loss of starting material occurs. However, it is preferable to strip the acid by-product from the reaction mixture, thus shifting the chemical equilibrium towards the formation of the desired chalcogenone product. It will be apparent that volatile acids such as acetic acid ($CH_3CO_2H$) are preferred for this purpose.

It will also be appreciated that ionic liquids and salts comprising heterocyclic cations may be obtained using "one-pot" syntheses, such as that described in U.S. Pat. No. 5,182,405. In accordance with a preferred embodiment of the invention, the synthesis of the ionic liquid or salt and subsequent formation of the heterocyclic chalcogenone according to the process of the invention, may be combined in a "one-pot" synthetic procedure.

Thus, for example, in accordance with this aspect of the present invention, and with reference to the method described in U.S. Pat. No. 5,182,405, an imidazole-2-chalcogenone of the formula (7):

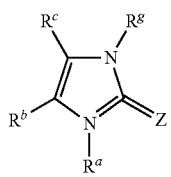

(7)

wherein: $R^a$, $R^b$, $R^c$ and $R^g$ are as defined above; and
Z is a sulphur, selenium or tellurium atom;
is obtainable by:
(i) reacting an α-dicarbonyl compound of the formula $R^b$—C(O)C(O)—$R^c$ with an amine of the formula $R^aNH_2$ (where $R^a=R^g$) or a mixture of amines $R^aNH_2$ and $R^gNH_2$ (where $R^a \neq R^g$), formaldehyde, and an acid [$H^+$][$X^-$] (wherein [$X^-$] is as defined above, that is, having a $pK_a$ of at least 2.5) to form a reaction mixture comprising an imidazolium ionic liquid or salt of the formula (8):

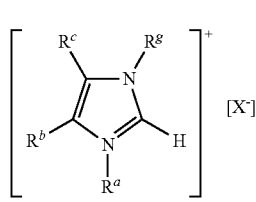

(8)

wherein: $R^a$, $R^b$, $R^c$ and $R^g$ are as defined above; and
[$X^-$] is as defined above; and
(ii) subsequently adding an elemental chalcogen selected from sulphur, selenium and tellurium directly to the reaction mixture from step (i).

Preferred definitions of $R^a$, $R^b$, $R^c$ and $R^g$ given above are also preferred in the context of this aspect of the invention.

In a further preferred embodiment, $R^a$ and $R^g$ are independently selected from ($C_1$ to $C_4$)alkyl, 2-hydroxyethyl or phenyl.

In a further preferred embodiment, $R^b$ and $R^c$ are independently selected from hydrogen, ($C_1$ to $C_4$)alkyl, or phenyl.

In a further preferred embodiment, [$X^-$] is selected from conjugate bases of acids [$H^+X^-$] having a $pK_a$ value greater than 2.5 and preferably less than 6. For example, [$X^-$] may be selected from [$CH_3CO_2$]$^-$, [$CH_3CH_2CO_2$]$^-$, [$CH_3(CH_2)_2CO_2$]$^-$, [$PhCO_2$]$^-$, and [$NO_2$]$^-$.

It will be appreciated that the above process may be adapted to form other heterocyclic chalcogenones, and that the selection of suitable starting materials, and reaction conditions, is within the knowledge of the person skilled in the art. In this regard, reference is made to the preferred embodiments disclosed above, for example, with respect to the first aspect of the invention.

The present invention will now be illustrated by way of the following examples:

EXAMPLES

Example 1

Approximately 3.1557 g (15.9 mmol) of colourless 1-butyl-3-methylimidazolium acetate were placed into a glass vial, and the stoichiometric amount of pale yellow sulfur (0.5095 g, 1.99 mmol, equivalent to 15.9 mmol of sulfur atoms) was added. The mixture was heated to 75° C. in the capped vial, and magnetically stirred. After approximately 1 minute, qualitative changes could be observed in the reaction medium. After approximately 10 minutes, the mixture looked dark brown, with some undissolved sulfur still observable at the bottom of the vial. The reaction was allowed to proceed for 48 h, after which a sample was withdrawn for analysis by $^1H$ and $^{13}C$ nuclear magnetic resonance (NMR) spectroscopy. The $^1H$ NMR spectrum showed the formation of a new species, in an approximated ratio 3:1 to the ionic liquid, with signals consistent with those reported in the literature for 1-butyl-3-methylimidazole-2-thione (Tao et al., *Syn. Commun.* 2007, 37, 399-408; Wolfe and Schreiner, *Eur. J. Org. Chem.* 2007, 2825-2838). The reaction medium was allowed to continue under the same conditions for 6 days, with no degradation observed in the ionic liquid; similar NMR spectra were obtained at this point, and an electrospray ionisation mass spectroscopy (ESI-MS) analysis further confirmed the presence of the thione.

Example 2

Approximately stoichiometric amounts of 1-ethyl-3-methylimidazolium acetate (2.0205 g, 11.9 mmol) and sulfur (0.3740 g, 1.46 mmol, equivalent to 11.7 mmol of sulfur atoms) were placed in a two-neck round-bottomed flask. A reflux condenser was attached to the main neck, whereas the auxiliary neck was simply stoppered. The mixture was stirred at a controlled temperature of 25° C. An evident change of colour of the mixture could be observed within the first minutes. Samples of the reaction medium were withdrawn for $^1H$ NMR analysis at different times over a period of 5 days. The signals were consistent with the formation of 1-ethyl-3-methylimidazole-2-thione, as reported in the literature (Tao et al., *Syn. Commun.* 2007, 37, 399-408). The integration of the spectra indicated that the reaction initially progresses fast, reaching a ca. 22% conversion of ionic liquid to thione right after 15 minutes from the start; but then it slows down, reaching a maximum conversion of ca. 47% within the first 24 h. For isolation of the thione formed, acetonitrile was added to the reacted medium. The unreacted sulfur did not dissolve, and it was filtered off. Then, the acetonitrile was removed, and water and dichloromethane were added. The organic phase was washed several times with fresh water, and finally the dichloromethane was removed under vacuum. The final sample was further purified under high vacuum, and it was characterised by gas chromatography mass spectroscopy (GC-MS), by ESI-MS and by $^1$H NMR and $^{13}$C NMR, all of the results indicating that the product was 1-ethyl-3-methylimidazole-2-thione.

Example 3

Imidazole (0.6864 g, 10.1 mmol) and acetic acid (0.6081 g, 10.1 mmol) were placed into a round-bottomed flask, stoppered, and stirred with heating for ca. 1 h. The liquid mixture was allowed to cool down, and sulfur (0.3280 g, 10.2 mmol S) was added in the stoichiometric amount, assuming the existence of a reaction for the formation of a thione via the combination of one atom of sulfur with the non-N-substituted ionic liquid presumably formed by imidazole and acetic acid (1-H-3-H-imidazolium acetate). This mixture was stirred at 25° C. for 4 days. At this point, a sample was withdrawn for analysis by $^1$H NMR spectroscopy. Contrary to the results in Example 1 and Example 2 with N-substituted imidazolium acetate ionic liquids, in this case no formation of the thione was observed at all.

Example 4

Sulfur (0.1457 g, 4.5 mmol) and 1-ethyl-3-methylimidazolium acetate (0.7683 g, 4.5 mmol) in stoichiometric amounts were mixed with twice the number of moles of acetic acid (0.5447 g, 9.1 mmol) in a round-bottomed flask, with a reflux condenser attached. The mixture was stirred at 25° C. for almost 2 days. The $^1$H NMR spectrum of the sample withdrawn from the medium was found to show the combination of the signals for the ionic liquid and the acetic acid, but no sign of thione formation. Thus, the presence of the acid has an inhibiting effect on the mechanism of reaction between the ionic liquid and sulfur.

Example 5

Water (0.5265 g) and 1-ethyl-3-methylimidazolium acetate (0.5226 g) were mixed in an approximately 50:50 w/w ratio, and sulfur in a 100% excess with regard to the amount of ionic liquid was added. The mixture was stirred at 25° C. for almost 2 days, and a sample was withdrawn for analysis. The $^1$H NMR spectrum indicated no formation of thione product. Therefore, the reaction between the ionic liquid and sulfur does not occur in aqueous medium. However, a reasonably small amount of water in the system is tolerable, as is proven by the fact that, in Example 1 and Example 2, the ionic liquids 1-butyl-3-methylimidazolium acetate and 1-ethyl-3-methylimidazolium acetate had measured water contents of 478 ppm and 516 ppm respectively.

The invention claimed is:

1. A process for the preparation of heterocyclic chalcogenone compounds comprising the reaction of an elemental chalcogen selected from the group consisting of elemental sulfur, elemental selenium and elemental tellurium with an ionic liquid or salt having the formula:

[Cat$^+$][X$^-$], wherein: [Cat$^+$] represents one or more heterocyclic cationic species of the general formula (1) having adjacent carbon and nitrogen atoms:

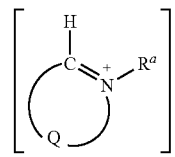

(1)

wherein $R^a$ represents a $C_1$ to $C_{30}$ straight chain or branched alkyl group, a $C_3$ to $C_8$ cycloalkyl group, a $C_6$ to $C_{10}$ aryl group, a $C_1$ to $C_{30}$ alkaryl group, or a $C_1$ to $C_{30}$ aralkyl group; wherein said alkyl, cycloalkyl, aryl, alkaryl or aralkyl groups are unsubstituted or substituted; and Q represents a linking moiety, which may be saturated or unsaturated, and which may be substituted or unsubstituted; and which when taken together with the adjacent carbon and nitrogen atoms forms a heterocyclic ring comprising 5 to 10 ring atoms; and

[X$^-$] represents one or more anionic species selected from conjugate bases of acids [H$^+$X$^-$] having a pK$_a$ value greater than 2.5; and wherein the reaction is conducted in the absence of an additional base.

2. The process according to claim 1, wherein the elemental chalcogen is selected from the group consisting of elemental selenium and elemental sulfur.

3. The process according to claim 2, wherein the elemental chalcogen is elemental sulfur.

4. The process according to claim 1, wherein general formula (1) represents a heterocyclic cationic ring structure selected from the group consisting of imidazolium, pyrazolium, 1,2,4-triazolium, oxazolium, isoxazolium, thiazolium, isothiazolium, 1,2,4-oxadiazolium, 1,2,5-oxadiazolium, 1,3,4-oxadiazolium, 1,2,3,4-oxatriazolium, 1,2,3,5-oxatriazolium, 1,2,4-thiadiazolium, 1,2,5-thiadiazolium, 1,3,4-thiadiazolium, 1,2,3,4-thiatriazolium, 1,2,3,5-thiatriazolium, pyridinium, pyridazinium, pyrimidinium, pyrazinium, 1,2,3-triazinium, 1,2,4-triazinium, 1,3,5-triazinium, 1H-indazolium, benzimidazolium, benzisoxazolium, benzoxazolium, benzothiazolium, benzisothiazolium, quinolinium, isoquinolinium, cinnolinium, quinazolinium, quinoxalinium, and phthalazinium.

5. The process according to claim 4, wherein general formula (1) represents a heterocyclic cationic ring structure selected from the group consisting of imidazolium, pyrazolium, 1,2,4-triazolium, oxazolium, thiazolium, pyridinium, pyridazinium, pyrimidinium, pyrazinium, benzimidazolium, quinolinium, and isoquinolinium.

6. The process according to claim 5, wherein general formula (1) represents a heterocyclic cationic ring structure selected from the group consisting of

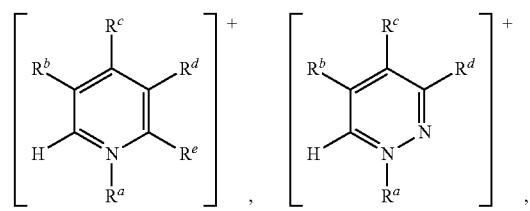

-continued

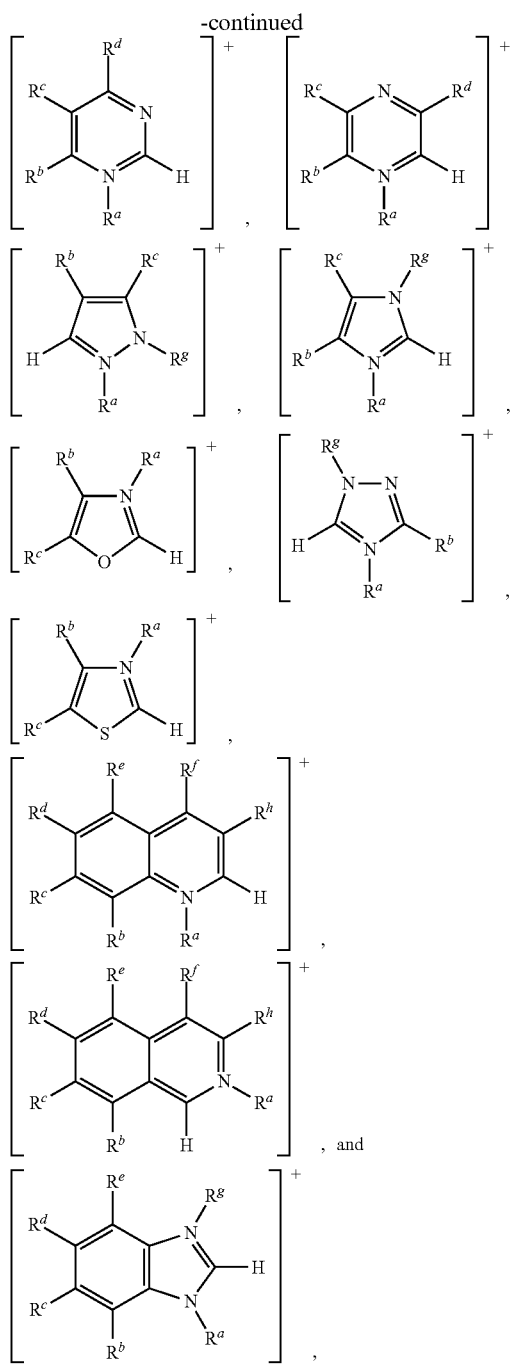

wherein: $R^a$, $R^b$, $R^c$, $R^d$, $R^e$, $R^f$, $R^g$ and $R^h$ are each independently selected from the group consisting of a $C_1$ to $C_{30}$, straight chain or branched alkyl group, a $C_3$ to $C_8$ cycloalkyl group, a $C_6$ to $C_{10}$ aryl group, $C_1$ to $C_{30}$ alkaryl group, a $C_1$ to $C_{30}$ aralkyl group, and wherein $R^b$, $R^c$, $R^d$, $R^e$, $R^f$ and $R^h$ may also be hydrogen or $C_1$ to $C_{30}$ alkoxy, or any two of $R^b$, $R^c$, $R^d$, $R^e$, $R^f$ and $R^h$ attached to adjacent carbon atoms may form a methylene chain —$(CH_2)_q$— wherein q is from 3 to 6; and wherein said alkyl, cycloalkyl, aryl, alkaryl, aralkyl or alkoxy groups or said methylene chain are unsubstituted or may be substituted by one to three groups selected from the group consisting of $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —$NO_2$, —$CO_2(C_1$ to $C_6)$alkyl, —$OC(O)R^x$, —$C(O)R^x$, —$C(S)R^x$, —$CS_2(C_1$ to $C_6)$alkyl, —$SC(S)R^x$, —$S(O)(C_1$ to $C_6)$alkyl, —$S(O)O(C_1$ to $C_6)$alkyl, —$OS(O)(C_1$ to $C_6)$alkyl, —$S(C_1$ to $C_6)$alkyl, —S—S$(C_1$ to $C_6$ alkyl), —$NR^xC(O)NR^yR^z$, —$NR^xC(O)O(C_1$ to $C_6)$alkyl, —$OC(O)NR^yR^z$, —$NR^xC(S)O(C_1$ to $C_6)$alkyl, —$OC(S)NR^yR^z$, —$NR^xC(S)S(C_1$ to $C_6)$alkyl, —$SC(S)NR^yR^z$, —$NR^xC(S)NR^yR^z$, —$C(O)NR^yR^z$, —$C(S)NR^yR^z$, —$NR^yR^z$, and a heterocyclic group, wherein $R^x$, $R^y$ and $R^z$ are independently selected from the group consisting of hydrogen and $C_1$ to $C_6$ alkyl.

7. The process according to claim 6, wherein general formula (1) represents a heterocyclic cationic ring structure selected from the group consisting of

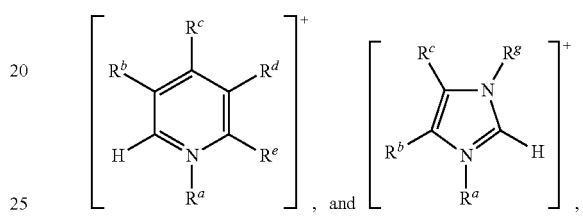

wherein: $R^a$, $R^b$, $R^c$, $R^d$, $R^e$, $R^f$, $R^g$ are as defined in claim 6.

8. A process according to claim 7, wherein general formula (1) represents a heterocyclic cationic ring structure selected from the group consisting of

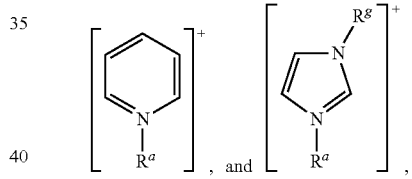

wherein: $R^a$ and $R^g$ are as defined in claim 6.

9. The process according to claim 1, wherein [X$^-$] comprises the anionic conjugate base of an acid [H$^+$X$^-$]having a pK$_a$ value greater than 3.5.

10. A process according to claim 1, wherein [X$^-$] comprises the anionic conjugate base of an acid [H$^+$X$^-$] having a pK$_a$ value greater than 4.5.

11. The process according to claim 1, wherein [X$^-$] comprises a carboxylate anion.

12. The process according to claim 11, wherein [X$^-$] comprises a carboxylate anion selected from the group consisting of [CH$_3$CO$_2$]$^-$, [CH$_3$CH$_2$CO$_2$]$^-$, [CH$_3$(CH$_2$)$_2$CO$_2$]$^-$,and [PhCO$_2$]$^-$.

13. The process according to claim 11, wherein [X$^-$] comprises an anion selected from the group consisting of [CN]$^-$, [CO$_3$]$^{2-}$, [HCO$_3$]$^-$, [OH]$^-$, [SH]$^-$, and [NO$_2$]$^-$.

14. The process according to claim 1, wherein the reaction is conducted at a temperature of from −10° C. to 150° C.

15. The process according to claim 14, wherein the reaction is conducted at a temperature of from 25° C. to 100° C.

16. The process according to claim 1, wherein the salt has a melting point below 150° C.

17. The process according to claim 16, wherein the salt has a melting point below 100° C.

18. The process according to claim 17, wherein the salt has a melting point below 25° C.

19. The process according to claim 1, wherein the salt is a solid at the operating temperature and pressure of the process.

20. The process according to claim 1, wherein the reaction is conducted in the presence of a solvent selected from the group consisting of acetonitrile, dimethylsulfoxide, dimethylformamide and sulfolane.

21. The process according to claim 1, wherein the reaction is conducted in the absence of an additional solvent.

22. The process according to claim 1, wherein the acid $[H^+X^-]$ is a by-product that is continuously removed from the reaction vessel.

23. The process according to claim 1, wherein the ionic liquid or salt and the chalcogen are reacted in a molar ratio, based on atoms of the chalcogen, of from 1:100 to 100:1.

24. The process according to claim 23, wherein the ionic liquid or salt and the chalcogen are reacted in a molar ratio, based on atoms of the chalcogen, of from 1:10 to 10:1.

25. The process according to claim 24, wherein the ionic liquid or salt and the chalcogen are reacted in a molar ratio, based on atoms of the chalcogen, of from 1:5 to 5:1.

26. The process according to claim 25, wherein the ionic liquid or salt and the chalcogen are reacted in a molar ratio, based on atoms of the chalcogen, of about 1:1.

27. The process according to claim 1, wherein the chalcogenone product is recovered from the reaction medium by solvent extraction using aqueous and/or organic solvents.

* * * * *